US010213190B2

(12) United States Patent
Dreyfus et al.

(10) Patent No.: US 10,213,190 B2
(45) Date of Patent: Feb. 26, 2019

(54) DEVICE FOR SAMPLING A BIOLOGICAL TISSUE

(71) Applicant: Commissariat à l'Energie Atomique et aux Energies Alternatives, Paris (FR)

(72) Inventors: Matthieu Dreyfus, Grenoble (FR); François Berger, Meylan (FR); Ali Bouamrani, Grenoble (FR); Adrien Mombrun, Grenoble (FR)

(73) Assignee: COMMISSARIAT A L'ENERGIE ATOMIQUE ET AUX ENERGIES ALTERNATIVES (FR)

( * ) Notice: Subject to any disclaimer, the term of this patent is extended or adjusted under 35 U.S.C. 154(b) by 105 days.

(21) Appl. No.: 14/585,361

(22) Filed: Dec. 30, 2014

(65) Prior Publication Data

US 2015/0182207 A1    Jul. 2, 2015

(30) Foreign Application Priority Data

Dec. 30, 2013   (FR) ...................... 13 63695

(51) Int. Cl.
*A61B 5/00* (2006.01)
*A61B 10/04* (2006.01)
(Continued)

(52) U.S. Cl.
CPC .......... *A61B 10/04* (2013.01); *A61B 1/00087* (2013.01); *A61B 1/00096* (2013.01);
(Continued)

(58) Field of Classification Search
CPC ............ A61B 1/00096; A61B 1/00117; A61B 1/00154; A61B 1/00167; A61B 1/00177;
(Continued)

(56) References Cited

U.S. PATENT DOCUMENTS 3,556,085 A  *  1/1971  Takahashi .......... A61B 1/00087
                                                            385/117
3,945,375 A      3/1976  Banko
                  (Continued)

FOREIGN PATENT DOCUMENTS

WO    2006082344 A1    8/2006
WO    2013091090 A1    6/2013
WO    2013098703 A1    7/2013

OTHER PUBLICATIONS

French Preliminary Search Report for Application No. FR 1363695 dated May 2, 2014.

*Primary Examiner* — May A Abouelela
(74) *Attorney, Agent, or Firm* — Lerner, David, Littenberg, Krumholz & Mentlik, LLP

(57) ABSTRACT

The invention relates to a device (100) for sampling a biological tissue comprising:
- a rod (1) extending along a longitudinal axis (X) between a proximal end (1a) and a distal end (1b),
- a capture surface (2) borne by the rod (1), intended to be applied against a biological tissue, wherein the capture surface is nanoporous or has protrusions adapted for sampling a biological tissue by micro abrasion,
- an observation window (3) transparent to visible light, laid out in the external surface of the rod (1),
- a housing (4) extending in the rod, parallel to the longitudinal axis, from the proximal end (1a) as far as the observation window (3) said housing being able to receive a bundle of optical fibers.

12 Claims, 3 Drawing Sheets

(51) Int. Cl.
*A61B 1/00* (2006.01)
*A61B 1/06* (2006.01)
*A61B 10/00* (2006.01)
*A61B 10/02* (2006.01)
*A61B 1/04* (2006.01)

(52) U.S. Cl.
CPC ...... *A61B 1/00154* (2013.01); *A61B 1/00167* (2013.01); *A61B 1/00177* (2013.01); *A61B 1/043* (2013.01); *A61B 1/0615* (2013.01); *A61B 5/0071* (2013.01); *A61B 5/0084* (2013.01); *A61B 10/0045* (2013.01); *A61B 10/02* (2013.01); *A61B 2010/0216* (2013.01); *H01L 2224/05624* (2013.01)

(58) Field of Classification Search
CPC ......... A61B 1/043; A61B 1/0615; A61B 1/07; A61B 5/0071; A61B 5/0075; A61B 5/0084; A61B 10/02; A61B 10/04; A61B 2010/0216; A61B 18/1492; A61B 1/0684; A61B 2018/00607; A61B 17/320016; A61B 2562/223; A61B 1/32; A61B 2017/003; A61B 2017/349; A61B 2018/00601; A61B 2018/1861; A61B 2018/2288; A61B 2090/3614
USPC ................ 600/562, 564, 566, 567, 570, 572
See application file for complete search history.

(56) References Cited

U.S. PATENT DOCUMENTS

| | | | | |
|---|---|---|---|---|
| 3,961,621 | A * | 6/1976 | Northeved | A61B 1/313 600/106 |
| 4,566,438 | A * | 1/1986 | Liese | A61B 5/0084 600/129 |
| 5,280,788 | A * | 1/1994 | Janes | A61B 5/0084 600/476 |
| 5,536,234 | A * | 7/1996 | Newman | A61B 1/00091 600/104 |
| 6,346,086 | B1 * | 2/2002 | Maksem | A61B 10/0291 600/569 |
| 6,564,087 | B1 * | 5/2003 | Pitris | A61B 1/00183 600/478 |
| 6,689,142 | B1 * | 2/2004 | Tremaglio, Jr. | A61B 17/3403 604/114 |
| 8,152,736 | B2 * | 4/2012 | Caillat | A61B 10/02 600/562 |
| 8,672,929 | B2 * | 3/2014 | Anderson | A61B 18/22 29/517 |
| 9,033,897 | B2 * | 5/2015 | Benabid | A61B 10/02 600/562 |
| 2009/0082695 | A1 * | 3/2009 | Whitehead | A61B 1/00052 600/562 |
| 2011/0112388 | A1 * | 5/2011 | Kuech | A61B 5/14546 600/341 |
| 2011/0176772 | A1 * | 7/2011 | Hixon | G02B 6/262 385/53 |

* cited by examiner

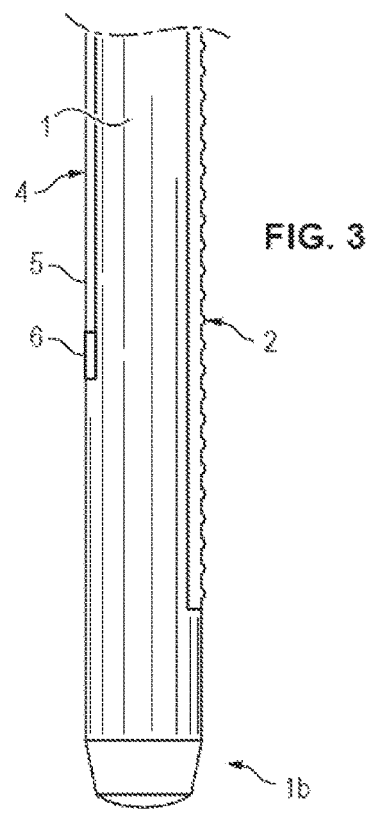
FIG. 3
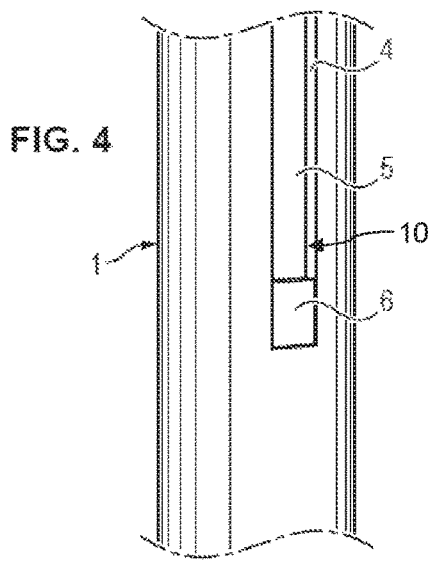
FIG. 4
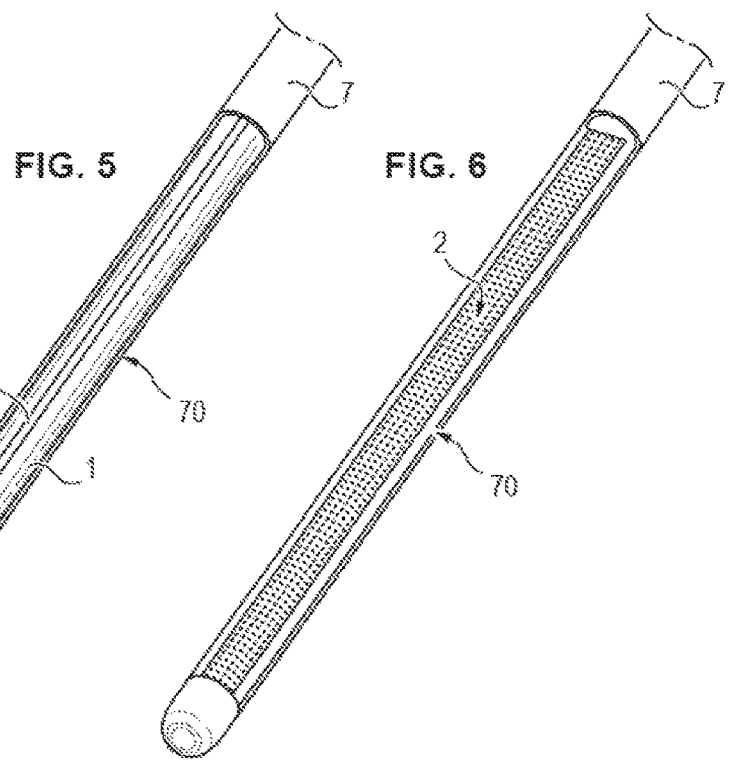
FIG. 5
FIG. 6

DEVICE FOR SAMPLING A BIOLOGICAL TISSUE

FIELD OF THE INVENTION

The present invention relates to a device for sampling a biological tissue.

BACKGROUND OF THE INVENTION

Sampling biological tissues in certain organs of a living being proves to be particularly complex because of the risks of damaging the organ in which the sample is taken.

This is for example the case of brain tumors, which are not very accessible to biopsy considering the incurred risks in terms of irreversible cognitive lesions.

Document WO 2006/082344 describes a minimally invasive sampling device which comprises a rod and a capture surface borne by the rod, intended to be applied against the biological tissue.

Document WO 2013/098703 describes a similar device, in which the capture surface includes a nanoporous material, and in particular nanoporous silicon.

By simple contact between the capture surface which is advantageously micro-structured or porous—and the tissue, a capture of cells and of macromolecules is obtained in territories of the nervous system inaccessible by surgery.

Considering the fact that the size of the tumor may be small, it is necessary that the capture surface be brought accurately at the tumor in order to sample the cells and macromolecules of interest.

However, accurate localization of the anatomic area where the sample is taken by means of this device is relatively complex, the practitioner not being able to directly view the organ in which it is introduced.

For this purpose, one possibility is to make the sampling device compatible with magnetic resonance imaging (MRI)—i.e. typically by making it in non-magnetic materials—which with this imaging technique gives the possibility of observing the introduction of the sampling device into the organ and checking the location of the capture surface.

However, applying the sampling under MRI poses difficulties in terms of availability of the equipment.

It would therefore be desirable to be able to proceed with a sampling of biological tissues in a specific area of an organ by doing it without magnetic resonance imaging.

SHORT DESCRIPTION OF THE INVENTION

An object of the invention is to design a minimally invasive device for sampling biological tissues which allows localization with improved accuracy of the area in which the sampling is carried out, without involving any external imaging system such as MRI.

According to the invention, a device for sampling a biological tissue is proposed, comprising:
- a rod extending along a longitudinal axis between a proximal end and a distal end,
- a capture surface borne by the rod, intended to be applied against a biological tissue, wherein the capture surface is nanoporous or has protrusions adapted for sampling a biological tissue by micro abrasion,
- an observation window transparent to visible light, laid out in the external surface of the rod,
- a housing extending in the rod, parallel to the longitudinal axis, from the proximal end as far as the observation window, said housing being able to receive a bundle of optical fibers.

Advantageously, the observation window and the capture surface are laid out at a same distance from the distal end of the rod and spaced apart angularly.

According to an embodiment, said housing of the bundle of optical fibers comprises a groove laid out in the external surface of the rod.

According to an embodiment, the device further comprises:
- a bundle of optical fibers positioned in the housing of the rod so that a distal end of said bundle is laid out in the vicinity of the observation window, and
- an optical return system adapted for producing optical coupling between the distal end of the bundle and the observation window.

According to an embodiment, the optical return system comprises a reflective plate orientated by an angle comprised between 40 and 50° relatively to the longitudinal axis of the rod.

Advantageously, said reflective plate is part of a prism.

According to the embodiment, the prism comprising said reflective plate is secured to the distal end of the bundle of optical fibers.

Alternatively, the optical return system consists in a beveled distal end of optical fibers forming the bundle.

The device may further comprise a guide tube in which the rod is able to slide, said guide tube comprising a side aperture laid out so that when the rod is introduced into the guide tube, the capture surface and the observation window will face said side aperture depending on the respective angular orientation of the guide tube and of the rod.

The capture surface is advantageously located in a distal region of the rod.

According to an embodiment, the capture surface is coated with a functionalization layer.

The rod is for example in stainless steel or in PEEK.

According to an advantageous embodiment, the cross section of the rod decreases from the proximal end to the distal end.

SHORT DESCRIPTION OF THE DRAWINGS

Other features and advantages of the invention will become apparent from the detailed description which follows, with reference to the appended drawings wherein:

FIG. 3 is a perspective side view of the rod,

FIG. 4 is a perspective view of the region of the observation window in the rod, FIG. 5 is a perspective view of the rod in the guide tube, in a position for observing the tissues, FIG. 6 is a perspective view of the rod in the guide tube, in a position for sampling a biological tissue.

DETAILED DESCRIPTION OF THE INVENTION

Figure 1:
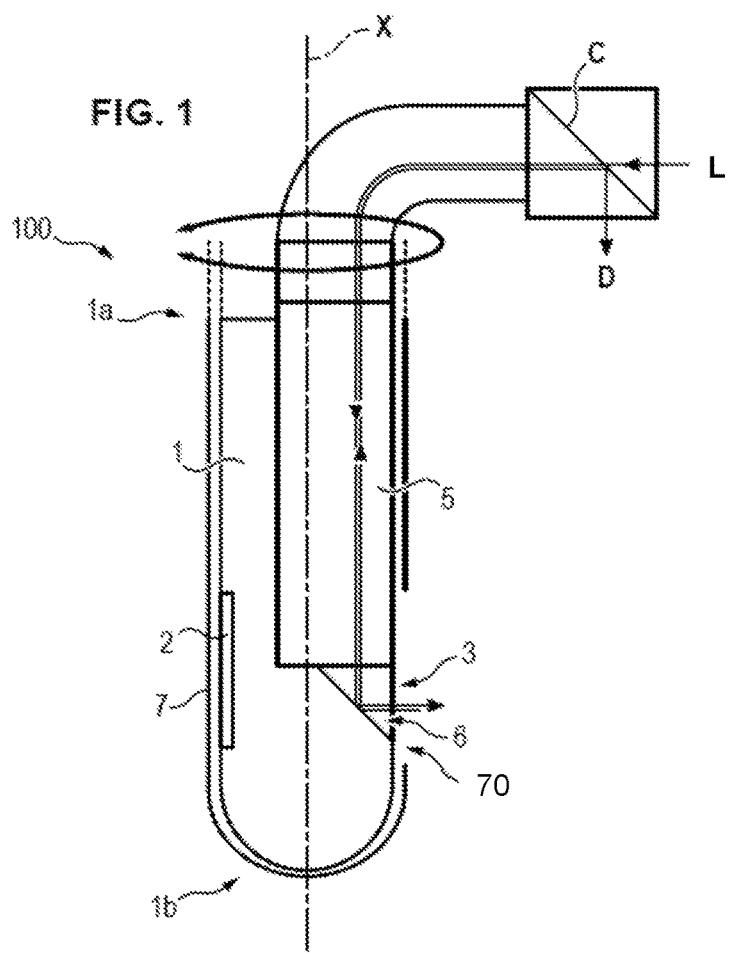
FIG. 1 is a sectional view of a sampling device according to an embodiment.

FIG. 1 is a sectional view of an embodiment of a device 100 for sampling biological tissues according to the invention.

The device 100 comprises a rod 1 which extends along a longitudinal axis X between a proximal end 1a and a distal end 1b. Conventionally, by "proximal" is meant the side which is closest to the hand of the practitioner and by "distal" is meant the side the furthest away, intended to come into contact with the tissues.

The rod 1 is made in a biocompatible material. The rod 1 may thus be made in stainless steel, or further in a plastic material such as PEEK (polyetheretherketone), which has the advantage, as compared with stainless steel, of being compatible with MRI.

The diameter of the rod is typically comprised between 500 µm and 2,000 µm, preferably between 800 µm and 1,200 µm. Advantageously, a diameter of 1,200 µm allows proper insertion into an existing guide tube.

Figure 7:
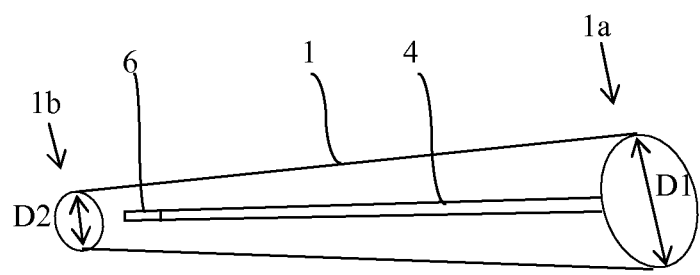
FIG. 7 is a perspective view of the rod according to an embodiment of the invention.

Preferably, the transversal cross section of the rod 1 decreases from the proximal end to the distal end. For example, as illustrated in FIG. 7, when the rod has a circular cross section, the diameter D2 of the distal end is smaller than the diameter D1 of the proximal end. Preferably, the diameter (or the diagonal if the cross section is not circular) of the distal end is three times smaller than the diameter (or the diagonal) of the proximal end. This allows a better handling of the rod by an operator, at the proximal end.

The rod 1 bears a capture surface 2 which is intended to be applied against a biological tissue at which a sample is desirably taken.

The capture surface 2 is generally a planar surface and with a rectangular contour, although it is not limited to this single shape. The length of the capture surface is preferably laid out parallel to the longitudinal axis.

The rod 1 may have a flat laid out at the periphery of the rod and on which is secured the capture surface, for example by adhesive bonding or by any other means. The connection of the capture surface relatively to the rod may either be removable or not. The flat is advantageously designed so that, when the capture surface 2 is assembled on the rod 1, it is included in the circular section of the rod and does not have any protrusion relatively to the peripheral surface of the rod.

While being planar at a macroscopic scale, the capture surface may be microstructured so as to have protrusions allowing sampling of a biological tissue by micro-abrasion. For example, said protrusions may consist in hexagonal pillars with a height of 50 µm and a diameter of 80 µm.

Alternatively, the capture surface may be the surface of a nanoporous material.

Silicon is frequently used as a capture surface material, regardless of the considered embodiment.

Moreover, the capture surface 2 may be coated with a functionalization layer promoting the grafting of analytes of interest. In the present text, the term «analyte» refers to a chemical or biological species, in particular a protein or a cell. The functionalization layer may notably be anionic layer.

Preferably, the capture surface 2 is located in a distal region of the rod 1.

Moreover, the rod 1 comprises an observation window 3 and a housing 4 extending in the rod from the proximal end 1a as far as said observation window. As this will be seen in detail below, said housing 4 is intended to receive a bundle of optical fibers.

By <<window>> in the present text is meant a surface adapted for transmitting visible light between the outer environment and the housing 4. Said window is therefore obtained by making an aperture between the external surface of the rod and the housing 4. The window may optionally be materialized by a material transparent to visible light; this material may be organic (such as Plexi® glass) or inorganic (such as glass). However, the presence of such a material is not indispensable and the window may simply consist in a free space between the outer surface of the rod 1 and the housing 4.

According to an embodiment, the housing 4 may consist in an orifice made in the thickness of the rod.

Alternatively, the housing 4 may consist in a groove 10 made in the external surface of the rod 1, which is generally easier to produce by machine. Said groove may for example have a square or rectangular section.

The dimensions of said groove are adapted to those of the bundle of optical fibers, so as to allow the insertion of said bundle into said groove. Preferably, the bundle of optical fibers is laid out removably in the housing; for example it is retained by clamping in the housing 4. The bundle may be partly inserted into the groove, i.e. a portion of the bundle extends beyond the walls of the groove; alternatively, the bundle is entirely housed in the groove, its external surface not jutting out from the cover defined by the walls of the groove.

When the bundle of optical fibers is totally inserted into the groove, the space left free in the groove around the bundle may be filled by means of a biocompatible polymer applied in the liquid state and then cured so as to form a confinement of the bundle of fibers. Preferably, said polymer further ensures continuity of the external surface of the rod in order to retain its circular section.

Said polymer is preferably an alginate, which is biocompatible and allows reversible filling of the groove. Indeed, this alginate may then be dissolved in a bath of a suitable solvent, which allows removal of the optical fibers from the groove.

The bundle of optical fibers 5 advantageously comprises about 3000 optical fibers laid out in a bundle with a circular section of a diameter of 0.3 mm. Such a bundle is the one fitting out the endoscope distributed by Mauna Kea Technologies under reference Cellvizio™.

The optical fibers are selected so as to guide any wavelength allowing spectral characterization of the biological tissues. Typically, the optical fibers have to guide a range of wavelengths comprised between the ultraviolet and the infrared, the latter having much better penetration into the tissues.

The bundle 5 has a proximal end which is connected to an excitation and detection system and a distal end which, when the bundle is in the position of use in the rod 1, is laid out in the vicinity of the observation window 3.

The device 100 moreover comprises an optical return system 6 adapted for producing optical coupling between the distal end of the bundle and the observation window. For this purpose, said system 6 is laid out in the vicinity of the window 3. The optical coupling system may be secured to the rod (for example it may be formed by a prism stuck to the distal end of the groove forming the housing 4, facing the observation window 3) or else, to the bundle of fibers, in which case it is attached to the distal end of this bundle.

According to an embodiment, the optical coupling system is formed by the end of the bundle which is cut as a bevel, the angle of the bevel being of the order of 40 to 50°, preferably 45°. According to this embodiment, the end of the bundle forms a tilted plane; thus, each fiber of the bundle is able to collect a light signal for which the angle of incidence is tilted relatively to the longitudinal axis of the bundle.

According to another embodiment, the optical return system is a reflective plate, orientated by about 40 to 50°, preferably 45° relatively to the longitudinal axis X.

Said reflective plate may belong to a prism, said prism being secured to the distal end of the bundle of optical fibers, for example by crimping, by adhesive bonding or by any other means. The prism typically has a square section, the length of which is equal to the diameter of the bundle of optical fibers.

Preferably, the optical return system is configured so as to divert the light emitted by the bundle of fibers along a direction substantially orthogonal to the longitudinal axis X. In this case, the bundle is able to collect, through its distal end, light for which the angle of incidence is orthogonal to the longitudinal axis X.

The device 100 advantageously comprises a guide tube 7 inside which the rod 1 may slide. The guide tube comprises a side aperture 70 so that when the rod is inserted into the tube the aperture 70 faces the portion of the rod which bears the capture surface and in which is made the observation window 3. The rod 1 is then free in translation and in rotation in the guide tube 7. This gives the possibility of placing, alternatively, the window 3 or the capture surface 2 facing the aperture 70, as detailed in the example described hereafter. The guide tube 7 has the function of protecting the rod and the capture surface, which may slide in the tube without being in contact with the tissues. The guide tube is in a biocompatible material such as stainless steel. The inner diameter of the guide tube is typically comprised between 1,000 and 3,000 µm, for example 1,200 µm.

When the rod has a decreasing cross section from its proximal end to its distal end (as shown in FIG. 7), the shape of the guide tube can be adapted accordingly. Therefore, the aperture of the guide tube, at its proximal end, is greater than at its distal end. The external geometry of the guide tube may also be discontinuous, the external diameter (or the diagonal if the cross section is not circular) of the proximal end being greater than the diameter (or the diagonal) of the distal end.

Figure 2:
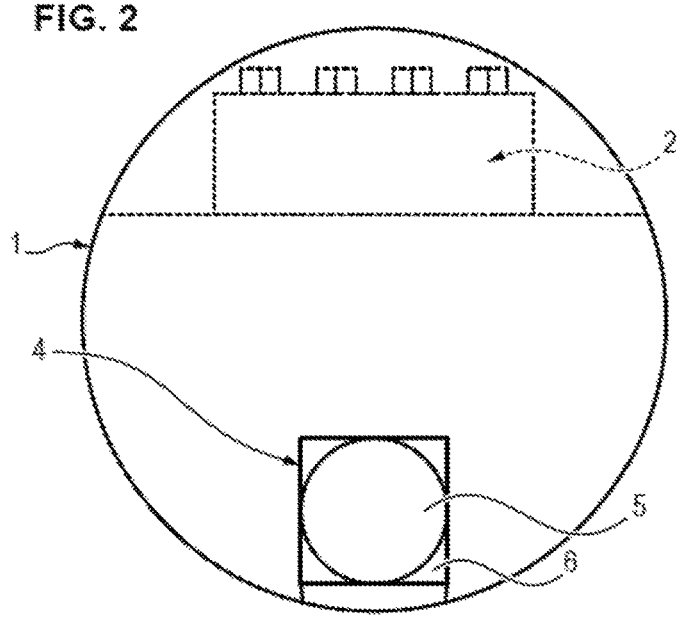
FIG. 2 is a front view of the proximal end of the rod of the sampling device.

FIG. 2 is a front view of the proximal end of the rod 1.

The housing 4 is in this case a groove with a rectangular section in which the bundle of optical fibers 5 is entirely contained. A prism 6 with a square base secured to the bundle is laid out at the distal end of the groove, facing the observation window (not shown here). Diametrically opposite to the groove 4 is laid out a flat bearing the capture surface 2, which here is microstructured by means of protruding pads.

FIG. 3 is a side view of the rod, the housing 4 being a groove diametrically opposite to the capture surface 2.

FIG. 4 is a view of the distal end of the groove, which contains the bundle 5 and an optical return system 6 laid out at the end of the bundle.

Now referring back to FIG. 1, the excitation and detection system typically comprises a light source L (for example a laser) and a photodetector D (preferably an array photodetector). The light source emits light at an excitation wavelength. The photodetector is laid out for detecting light at an emission wavelength, the latter being notably produced by a biological tissue in response to the excitation light. The proximal end of the bundle, the light source and the photodetector are advantageously coupled by an optical coupling system C, for example a dichroic mirror.

The photodetector is preferably coupled with a filter, for example an interferential filter, the bandwidth of which is centered on the fluorescent wavelength, emission wavelength. This filter may be placed on the dichroic mirror, or between the latter and the photodetector.

For implementing a sampling operation, the rod 1 is laid out in the guide tube 7 so that the observation window is facing the aperture 70 (c.f. FIG. 5).

As the bundle is in position in its housing of the rod, the optical fibers collect the excitation light signal emitted by the light source L which is coupled with the proximal end of the bundle as far as the distal end of the bundle. The signal is diverted by the optical return system 6 and transmitted to the outer environment of the tube through the observation window 3. Thus, the signal will excite fluorescent markers which have been injected beforehand into the patient who has to be subject to the sampling, or endogenous fluorescent markers, naturally present in the biological tissues.

Said markers then emit a fluorescent signal, which is transmitted through the observation window 3, diverted by the optical return system 6 and led by the optical fibers as far as the photodetector D through the optical coupling system C, following the reverse path of that of the excitation signal.

The bundle of optical fibers thus ensures two functions:
illuminating the tissues illuminated through the observation window 3 on the one hand;
collecting a fluorescent signal emitted by the illuminated tissues on the other hand.

The photodetector is adapted for detecting a fluorescent signal emitted by the tissues and therefore an indicator of the presence or not of the tissues of interest, the latter generating a fluorescent signal detectable by the photodetector D.

If the analysis carried out by the photodetector shows that the device is located in a favorable region, the practitioner brings the capture surface 2 facing the aperture 70 in order to put it into contact with the tissue (c.f. FIG. 6).

Preferably, the observation window 3 is located in the same longitudinal position of the rod as the capture surface but angularly shifted. This angular shift is for example of 180° (the capture surface and the observation window being diametrically opposite) but any other angle may be selected. Advantageously, the device comprises an angular indexation system which allows it to easily position either the observation window 3 or the capture surface 2 facing the aperture 70 of the guide tube 7. Thus, once the device is in place in a region favorable for the sampling, the practitioner immobilizes the guide tube 7 and contents himself/herself with pivoting the rod 1 for bringing the capture surface 2. He/she is thus certain of carrying out the sampling in the same region as the one which he/she has observed and selected.

If necessary, several samplings may be carried out in the same region: for this purpose it is sufficient to remove from the guide tube the rod bearing the capture surface on which a sample has been taken and of inserting a new rod bearing a blank capture surface.

Moreover, once the guide tube has been positioned in the desired region, it is possible to remove the bundle of optical fibers of the rod and insert into the guide tube the rod only provided with the capture surface.

Finally, the handling of the sampling device by a surgeon was mentioned but it is also possible that the device be manipulated by a robot.

REFERENCES

WO 2006/082344
WO 2013/098703

The invention claimed is:
1. A device for sampling a biological tissue comprising: a rod extending along a longitudinal axis between a proximal end and a distal end, and a guide tube in which the rod is slidably and rotatably arranged therein, comprising a side aperture, wherein the rod comprises an external surface facing an inner surface of the guide tube, a capture surface configured to be applied against a biological tissue, wherein the capture surface is nanoporous or has protrusions adapted for sampling a biological tissue by micro abrasion, an observation window transparent to visible light, laid out in the external surface, and a longitudinal groove extending into the external surface of the rod, from the proximal end of the rod to the observation window, said groove being configured to receive a bundle of optical fibers, wherein the observation window and the capture surface are laid out at a same distance from the distal end of the rod and spaced out angularly, so that one of the capture surface and the observation window may face the side aperture depending on the respective angular orientation of the guide tube and of the rod.

2. The device of claim 1, further comprising the bundle of optical fibers arranged within the groove with a distal end of said bundle laid out in a vicinity of the observation window.

3. The device of claim 1, further comprising:

an optical return system adapted for producing optical coupling between the distal end of the bundle and a distal end of the observation window.

4. The device of claim 3, wherein the optical return system comprises a reflective plate orientated by an angle between 40 and 50° relatively to the longitudinal axis of the rod.

5. The device of claim 4, wherein the reflective plate is part of a prism.

6. The device of claim 5, wherein the prism comprising the reflective plate is secured to the distal end of the bundle of optical fibers.

7. The device of claim 3, wherein the bundle of optical fibers comprises a beveled distal end, the beveled distal end forming the optical return system.

8. The device of claim 1, further comprising the guide tube in which the rod is able to slide therein, said guide tube comprising the side aperture laid out so that, when the rod is introduced into the guide tube, one of the capture surface and the observation window face said side aperture depending on a respective angular orientation of the guide tube and of the rod.

9. The device of claim 1, wherein the capture surface is located in a distal region of the rod.

10. The device of claim 1, wherein the capture surface is coated with a functionalization layer.

11. The device of claim 1, wherein the rod is made from stainless steel or PEEK.

12. The device of claim 1, wherein a cross section of the rod decreases from the proximal end to the distal end.

* * * * *